United States Patent [19]

Kloth et al.

[11] Patent Number: 4,964,728
[45] Date of Patent: Oct. 23, 1990

[54] BLOOD COAGULATION TIME MEASURING DEVICE

[75] Inventors: Bernd Kloth; Holger Behnk, both of Hamburg, Fed. Rep. of Germany

[73] Assignee: Firma Labor Laborgeräte'Analysensysteme Vertriebsgesellschaft mbH, Hamburg, Fed. Rep. of Germany

[21] Appl. No.: 317,123

[22] Filed: Mar. 1, 1989

Related U.S. Application Data

[63] Continuation-in-part of Ser. No. 774,176, Sep. 9, 1985, abandoned, which is a continuation of Ser. No. 663,830, Oct. 23, 1984, abandoned, which is a continuation-in-part of Ser. No. 452,784, Dec. 27, 1982, abandoned, which is a continuation of Ser. No. 381,467, May 24, 1982, abandoned, which is a continuation of Ser. No. 101,078, Dec. 7, 1979, abandoned, which is a continuation of Ser. No. 876,507, Feb. 9, 1978, abandoned.

[30] Foreign Application Priority Data

Mar. 11, 1977 [DE] Fed. Rep. of Germany ... 7707546[U]

[51] Int. Cl.⁵ ............................................. G01N 21/59
[52] U.S. Cl. ......................................... 356/427; 422/73
[58] Field of Search ........................ 250/238, 239, 576; 356/39, 73, 426, 427, 432, 436–438, 441, 442; 422/73

[56] References Cited

U.S. PATENT DOCUMENTS

| | | |
|---|---|---|
| 3,307,392 | 3/1967 | Owen et al. ............... 422/73 X |
| 3,520,659 | 7/1970 | Steinberg et al. |
| 3,736,431 | 5/1973 | Childs .............................. 356/442 |
| 3,847,482 | 11/1974 | Sokol et al. .................... 356/244 X |
| 3,936,192 | 2/1976 | Skala ................................ 356/442 |
| 3,989,382 | 11/1976 | Kent et al. ........................ 356/39 |
| 4,116,564 | 9/1978 | Renaud et al. ................. 356/39 X |

FOREIGN PATENT DOCUMENTS

| | | |
|---|---|---|
| 1930270 | 12/1969 | Fed. Rep. of Germany . |
| 2009524 | 2/1970 | France . |
| 2089651 | 1/1972 | France . |
| 2163483 | 7/1973 | France . |
| 2301011 | 9/1976 | France . |

*Primary Examiner*—Bruce Y. Arnold
*Attorney, Agent, or Firm*—Toren, McGeady & Associates

[57] ABSTRACT

A blood coagulation time measuring device includes a stirrer drive arrangement for rotating a stirring rod placed inside the measuring vessel when the vessel is inserted in a measuring channel of the device. A light detector assembly within the device determines the degree of coagulation formation in the measuring vessel by transmitting a light beam from a light source through the measuring vessel and onto a photo-electric cell. Light balancing circuitry coupled to the light source and the photo-electric cell automatically adjusts the brightness of the light from the light source in correspondence with the turbidity of liquid in the measuring vessel. A control switch arrangement operates to turn the stirrer drive arrangement on or off in response to operation of the light balancing circuitry.

6 Claims, 2 Drawing Sheets

BLOOD COAGULATION TIME MEASURING DEVICE

This is a continuation-in-part application of Ser. No. 774,176, filed Sept. 9, 1985, which in turn is a continuation application of Ser. No. 663,830, filed Oct. 23, 1984, which in turn is a continuation-in-part application of Ser. No. 452,784, filed Dec. 27, 1982, which in turn is a continuation application of Ser. No. 381,467, filed May 24, 1982, which in turn is a continuation application of Ser. No. 101,078, filed Dec. 7, 1979, and which in turn is a continuation application of Ser. No. 876,507, filed Feb. 9, 1978, all now abandoned.

BACKGROUND OF THE INVENTION

The invention relates to a blood coagulation time measuring device which provides a digital display of the coagulation time, and is capable of permitting the use of reagents and plasmas of varying turbidity and/or whole blood.

Various constructions of devices for determining and measuring blood coagulation time are known. In one known construction, a mechanical stirring device is provided in which two hook-like stirrers permit a thorough mixing of the reagents and plasma until fibrin fibers are formed, such mixing continuing up to the time when the fibrin fibers cohere between the hooks. Conductivity measurements are then carried out. However, in the case of a low fibrin concentration or when there is a flocculation of the plasma, no conductivity changes are obtained, thus making precise measurements impossible.

SUMMARY OF THE INVENTION

An object of the present invention is to provide a blood coagulation time measuring device which permits a thorough mixing of reagents and plasma while detecting light transmitted through the coagulum formation and which device makes possible an automatic light transmission level balance even when using reagents of varying turbidity, plasma and whole blood.

Another object of the invention is to provide a blood coagulation time measuring device which permits the elimination of intermediate turbidity, e.g., in the oxalate plasma method, as well as problems due to insoluble reagent or plasma particles in the threshold range.

According to the invention, a blood coagulation time measuring device which provides a digital display of the coagulation time, comprises a container having a measuring channel extending into the interior of the container, stirrer drive means in the region of the measuring channel for rotating a stirring rod inside a measuring vessel placed in the measuring channel, a light detector assembly in the container for determining coagulation formation by transmitting a light beam from a light source through the measuring vessel and onto a photo-electric cell which produces a corresponding output, light balancing means coupled to the light source and the photo-electric cell for adjusting the brightness of the light beam from the light source in corresponding relationship to the level of light directed onto the photo-electric cell, and control switch means coupled to the light balancing means for controlling the stirrer drive means in response to operation of the light balancing means.

The present blood coagulation time measuring device permits the thorough mixing of reagent and plasma in the measuring vessel simultaneously with light scanning of the coagulum formation. Automatic light transmission balancing permits the use of reagents and plasmas of varying turbidity and/or whole blood. Two threshold value limits can be set to ensure that the stirrer drive means of the device ceases to operate when light transmission through the vessel increases or decreases with respect to such limits. In addition, the device eliminates intermediate turbidity, as well as problems resulting from insoluble reagent and plasma particles in the threshold range.

The present device also has a high sensitivity even in the case of low fibrinogen concentrations. It is possible, for example, to determine all plasma coagulation times such as quick, PTT, thrombin time, plasma recalcification, fibrinogen and the like. Accurate values are still obtained if a strong or weak fibrin concentration is present. The turbidity which occurs with pronounced fibrin cross-linking initiates the switching off of the device in the same way as a low fibrin concentration and the associated flocculation.

For a better understanding of the present invention, reference is made to the following description and accompanying drawing, while the scope of the present invention will be pointed out in the appended claims.

DETAILED DESCRIPTION OF THE INVENTION

Figure 1:
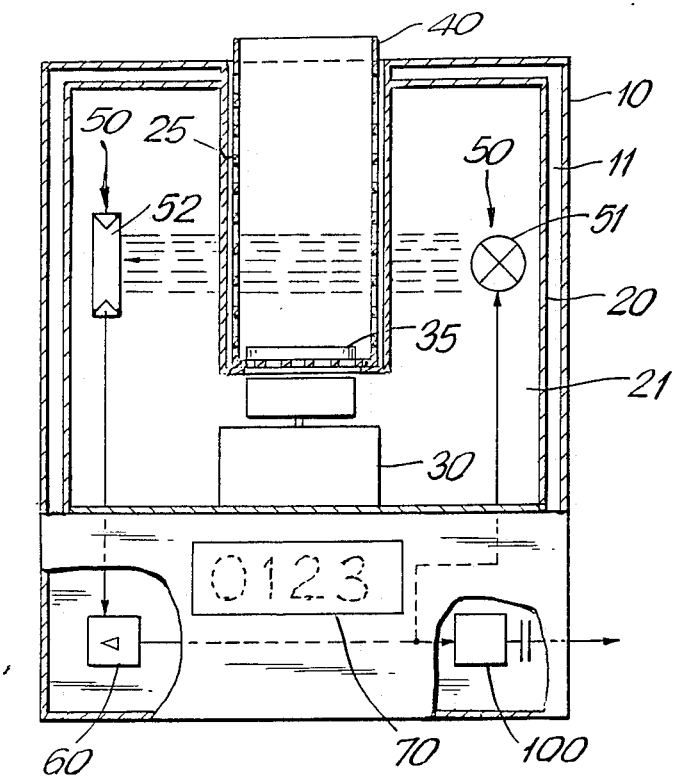
FIG. 1 shows, partly in elevation and partly in vertical section, an embodiment of a blood coagulation time measuring device in accordance with the invention.

The present blood coagulation time measuring device comprises a box-like housing 10 made from plastics or other suitable materials. A temperature-controllable metal container 20 is arranged in the interior 11 of the housing 10. Housing 10 and metal container 20 are joined at the top by an elongated measuring channel 25 which is arranged to receive a cylindrical measuring vessel 40, and which channel projects into the interior 21 of the metal container 20.

Measuring channel 25 has a bottom end wall located above a magnetic stirrer mechanism 30 arranged in the interior 21 of metal container 20. The stirrer mechanism 30 serves to rotate a stirring rod 35 located in and near the bottom of the measuring vessel 40. However, it is also possible to arrange the magnetic stirrer mechanism 30 in housing 10 wherein the metal container 20 would be provided with an opening (not shown) in the region of the stirrer mechanism 30.

Measuring vessel 40 is held in measuring channel 25 in such a way that the stirring rod 35 at the bottom of the vessel can be rotated by the magnetic stirrer mechanism 30, wherein the latter may be a drive mechanism which produces a rotary magnetic field. It is also possible to use devices in which a permanent magnet is driven to rotate in a horizontal plane so as to move the stirring rod 35 in the vessel 40. The stirring rod 35 is made from iron or may comprise a permanent magnet.

A light detector assembly 50, comprising a light source 51 and a photo-electric cell 52, is arranged in the interior of the metal container 20, in the vicinity of the measuring channel 25 and measuring vessel 40. The arrangement of the light detector assembly 50 is such that the beam path passing through the vessel is in no way impaired by the walls of channel 25, and passes above the stirring rod 35 which lies at the bottom of the vessel 40 to be driven by the magnetic stirrer mechanism 30. The measuring channel 25 may be provided with openings in the path of the light beam from the light detector assembly. Further, the walls of measuring channel 25 also may be made from light-permeable materials. It is also possible to provide rodshaped mounting supports for the measuring vessel 40, which in no way influence the light beam between light source 51 and photo-electric cell 52 as the beam passes through the vessel 40.

Photo-electric cell 52 of the light detector assembly 50 is connected via an amplifier 60 with a control switch mechanism 100, by means of which the magnetic stirrer mechanism 30 is switched on and off. The magnetic stirrer mechanism 30 is turned on by the control switch mechanism 100 when a predetermined start signal is produced by the photo-electric cell 52 of the light detector assembly 50 and applied to the switch mechanism 100 through the amplifier 60. The magnetic stirrer mechanism 30 is turned off in the same manner when a predetermined stop signal is produced and applied to the switch mechanism 100. The magnetic stirrer mechanism 30 may be constructed so that, after a specific time has expired, the stirring speed is reduced by means of a conventional internal timing device so as not to destroy unstable coagulum formations during long clotting times, e.g., in excess of 40 seconds.

Figure 2A:
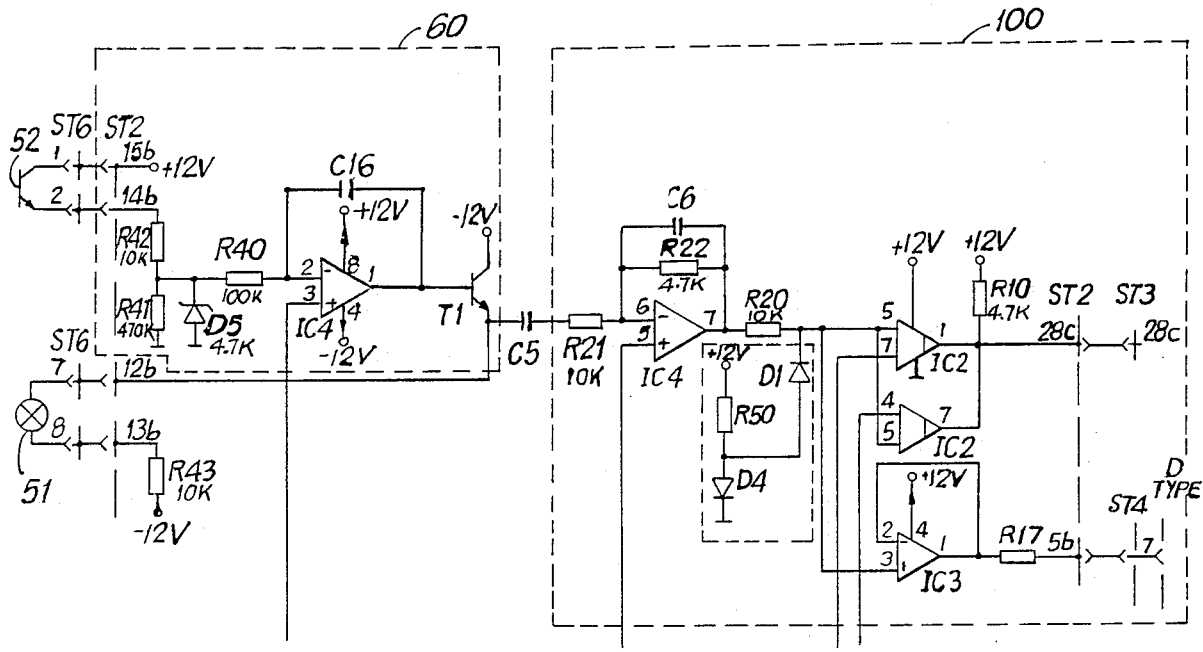
FIG. 2a shows a circuit portion corresponding to the amplifier 60 in FIG. 1.

In FIG. 2a, the photoelectric cell 52 is a phototransistor. The resistances R42 and R41 merely serves in connection with a Zener diode D5, to protect the input of the operational magnifier IC4 from excessively high voltage peaks. Because of the action of the Zener diode D5, the inverted input terminal 2 of the left portion of the IC4 (the utilized IC TL082 is a dual operational amplifier) lies at voltages between $-0.7$ and $+4.7$ volts. Depending upon whether the signal at the inverted input terminal is larger than that at the non-inverted input terminal vice versa, the light source 51 is switched off or on by means of the power transistor BD675.

The above-described portion of the circuit corresponds to the amplifier 60 in FIG. 1.

The output signal of the amplifier 60 is further utilized through the differentiating member C5, R21 as a start/stop signal. The positive circuit portion generated when the lamp is switched on serves here as a start signal; the negative circuit portion generated when the lamp is switched off serves as a stop signal.

The time constant of the integrating link formed by C6, R22 and the right-hand portion IC4 is smaller than that of the differentiating link C5, R21. In this way, interfering pulses of short duration are filtered out. The circuit portion formed by D1, D4 and R50 is an additional protective circuit, with which it is intended to be avoided that less than 0 volts be applied at the inputs of the following comparators.

Since the ICLM339 exhibits a so-called "open collector " - output, the output at the terminal 28c is always then logically "0", if one of the comparator conditions for the operational amplifier of the IC 2 switched as comparator is met. This would occur, then, if the level of the input signal is within the range of 5.5 V or 5.6 V to 6.5 V or 6.4 V, or if it is outside of this level. This serves for switching-off the motor, if too much or too little light impinges upon the photodetector 52.

In such case, a time-measuring device is connected to the terminal 5b, which measures the blood coagulation time.

Figure 2B:
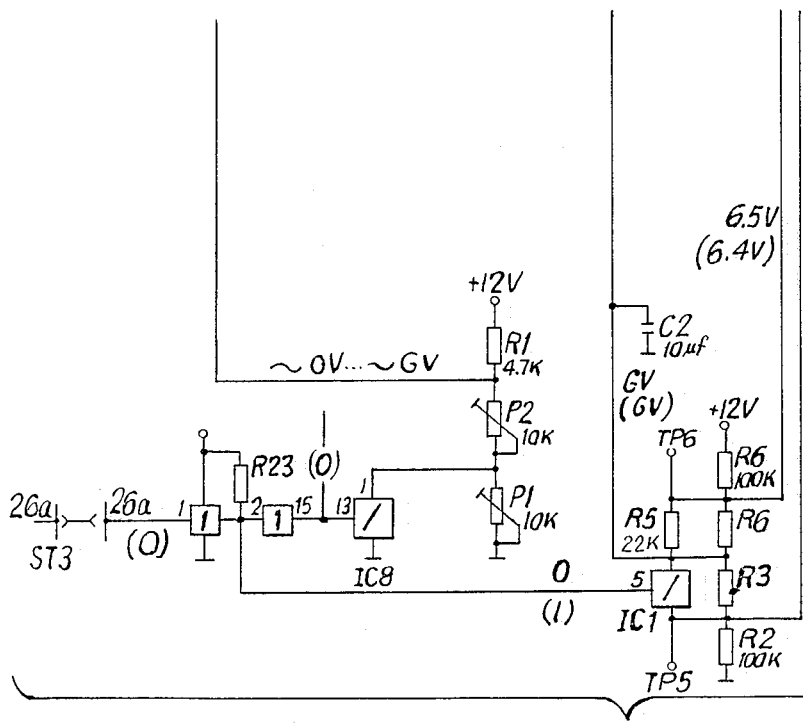
FIG. 2b shows a switching circuit.

In FIG. 2b, the IC4066 element is a so-called analog switch, whereby the terminal conditions are indicated on the right-hand side in FIG. 2b. With switches of this type, selectively specific analog voltages are transmitted to an output.

The terminal designated by 26a is a control input. Since, here, the voltage of the non-inverted input terminal of the left operational amplifier of IC4 (see FIG. 2a) and with it the switching threshold of this operational amplifier is influenced, as is further shown below, the voltage reduction mentioned in the description serves for preservation of the lamp when the measuring cuvette is removed. This reduction occurs automatically since the amplifier 60 forms a closed regulation circuit between the light source and the photoelectric cell. Voltage reduction should automatically occur, when the measuring cuvette is removed, therefore when the photoelectric cell is illuminated more strongly by the light source.

Terminal 26a is a digital input, whose input signal is conducted directly to an inverter, whose input is again connected with an inverter and with the switch input of a switch in the analog switch 4066. The output of the second inverter, at which in principle the same signals as at the terminal 26a are present, is connected with the switch input of another switch from the IC4066. By means of this analog switch, the potentiometer P1 is short-circuited, if a logic "1" is present at the input terminal 26a. Hereby, at the same time, the voltage at the point of connection between R1 and P2 is lowered. The degree of voltage drop and naturally also the original voltage is greatly depending on the adjustment of the potentiometers P2 and P1. The drawn-in voltages without brackets are present then, if the logic level at the input terminal 26a is "1?, while the voltage and logic values in brackets are present if this input terminal exhibits the logic value "0".

With the right-hand side of the circuit in FIG. 2b, a minimal change of range of the switching range for the comparators in IC2 (FIG. 2a) is achieved.

Figure 3:
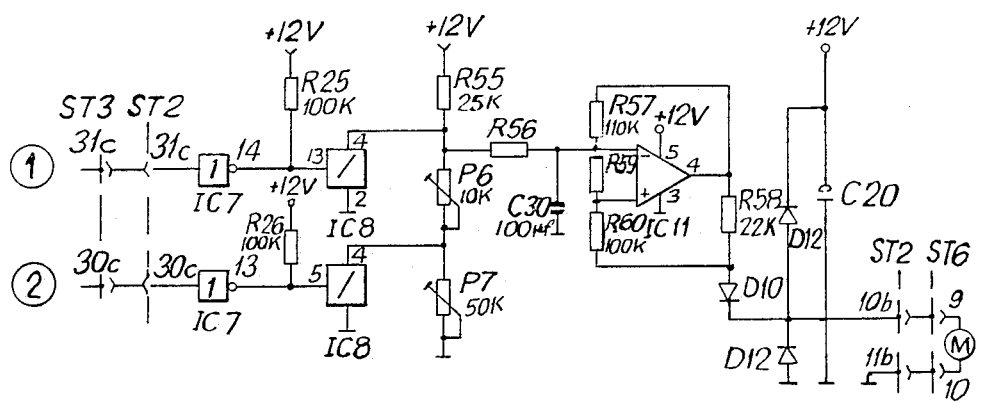
FIG. 3 shows a circuit for adjusting motor speed.

FIG. 3 indicates a circuit for adjusting the motor speed. The digital input signals determine the motor speed. Because of the integrating link R56, C30, the adaptation of a newly selected speed occurs with a specific time constant which can be adjusted by P6 and P7. The stirring motor M is directly connected to this circuit.

Sensitive working is ensured by the light detection of the coagulation process, while the magnetic stirrer mechanism 30 permits a reliable transition to coagulation.

A conventional digital display 70 is provided for reading off the coagulation time values.

The brightness of the light source 51 is automatically balanced as a function of the turbidity level of the liquid to be measured. It is thus possible for the photo-electric cell 52 always to work in a specific optimum range of its characteristic.

The beginning and end of the measuring time period is effected by a balancing arrangement wherein a primary change in one sense of the optic transmission in the vessel 40 causes secondarily a change in the opposite sense of the lamp voltage. That is, as the turbidity of the mixture in the vessel 40 increases so that light transmission through the vessel decreases, the lamp voltage is increased to balance or compensate for the increased turbidity, e.g., maintain a constant light level on the photo-electric cell 52.

The start and the stop signal levels can be determined within the range of variation of the lamp voltage, and the measuring time and the magnetic stirrer mechanism 30 each can be correspondingly started or stopped. In the case of an empty measuring vessel, suitable means may cause the lamp voltage to drop to 30% of the nominal voltage so that the service life of the lamp is considerably increased.

Due to the above brightness balancing arrangement, the measuring process is to a great extent independent from the absolute, optic transmission (turbidity) of the reagents and plasma in the measuring vessel 40 because the measuring process produces signals which correspond only to the change of the optic transmission, from the start of transmission through the sample and reagent. The range to which the light detector assembly 50 automatically adjusts, extends from reagents to whole blood. The brightness balance over the entire turbidity level of 0-100% T may take place during a maximum period of ten seconds. Then, the digital indicator 70 may show that the light detector 50 has completed a brightness balance, and a start signal may once again be triggered upon adding plasma or reagent so as to initiate a new brightness balance operation. The initially obtained light transmission level is continuously compared with that obtained during the measuring time of coagulation, for a subsequent increase or decrease. Five seconds after the start of the measuring time, a change in the light transmission level beyond preset threshold value limits may serve to terminate the measuring time period.

To ensure that the present device is turned off by means of the control switch mechanism 100 if the light transmission level increases or decreases, such increase or decrease of transmission level relative to the starting transmission level are derived independently from one another by appropriate circuitry. By means of an OR-gate arrangement, either an increase or decrease of the light transmission level can trigger the start or stop signal when a preset threshold value is exceeded or no longer maintained.

The invention is not restricted to the embodiment herein described and represented in the drawing. Modifications to the construction of the housing of the device, and the positioning of the temperature-controllable metal container in the interior of the housing are intended to be within the scope of the invention as would be a different position of the digital display device relative to the housing.

While the foregoing description and drawing represent the preferred embodiments of the present invention, it will be obvious to those skilled in the art that various changes and modifications may be made therein without departing from the true spirit and scope of the present invention.

We claim:

1. A blood coagulation time measuring device, comprising a container, channel means extending into said container for forming a measuring channel for supporting a measuring vessel within said container, stirrer drive means in the region of said channel means for rotating a stirring rod placed inside the measuring vessel, a light detector assembly in said container including a light source and a photo-electric cell for determining the degree of coagulum formation in the measuring vessel wherein a light beam is transmitted from said light source through the measuring vessel in said measuring channel and onto said photo-electric cell which produces a corresponding output, light balancing means coupled to said light source and said photo-electric cell for adjusting the brightness of the light beam from said light source in corresponding relationship to the level of light received by said photo-electric cell wherein said brightness corresponds to the turbidity of liquid in the measuring vessel, display means for indicating blood coagulation time, and control switch means coupled to said light balancing means for controlling said stirrer drive means and said display means in response to operation of said light balancing means.

2. A blood coagulation time measuring device according to claim 1, wherein said light balancing means is arranged so that first and second threshold values corresponding to different liquid turbidity levels can be set wherein said stirrer drive means operates when the turbidity of liquid in the vessel exceeds said first threshold value and is less than said second threshold value, and said stirrer drive means ceases to operate when the liquid turbidity exceeds said second threshold value.

3. A blood coagulation time measuring device according to claim 1, including a timing device associated with said stirrer drive means for reducing the speed of rotation of the stirring rod in the measuring vessel at a certain time after said stirrer drive means is activated by said control switch means.

4. A blood coagulation time measuring device according to claim 1, wherein said light balancing means includes an amplifier.

5. A blood coagulation time measuring device according to claim 1, wherein said light source comprises an electric lamp arranged to provide full brightness at a certain operating voltage, and said light balancing means is arranged to apply about 30% of said operating voltage to said lamp when the measuring vessel in said measuring channel is empty.

6. A blood coagulation time measuring device according to claim 1, wherein said light source comprises an electric lamp, said light balancing means operates to vary the voltage applied to said lamp over a certain range in accordance with the output of said photo-electric cell, and said control switch means is arranged to operate when the voltage applied to said lamp is between predetermined limits within said certain range of voltage.

* * * * *